United States Patent [19]

Ajagu et al.

[11] Patent Number: 4,475,392
[45] Date of Patent: Oct. 9, 1984

[54] SKIN FRICTION GAGE FOR TIME-RESOLVED MEASUREMENTS

[75] Inventors: Christopher O. Ajagu, Palo Alto; Paul A. Libby, La Jolla; John C. LaRue, Irvine, all of Calif.

[73] Assignee: The Regents of the University of California, Berkeley, Calif.

[21] Appl. No.: 474,141

[22] Filed: Mar. 10, 1983

[51] Int. Cl.³ .................... G01K 3/00; G01D 21/00
[52] U.S. Cl. ................................ 73/432 R; 73/204; 374/54
[58] Field of Search ............. 73/204, 432 R; 374/54

[56] References Cited

U.S. PATENT DOCUMENTS 4,061,029 12/1977 Fletcher .......................... 73/180
4,317,102 2/1982 Vranas .............................. 338/28

OTHER PUBLICATIONS

Liepmann et al., "Shearing-Stress Measurments by Use of a Heated Element," National Advisory Committee of Aeronautics Technical Note 3268 (1954).
Rubesin et al., "A Hot-Wire Surface Gage for Skin Friction and Separation Detection Measurments," NASA Technical Memorandum TM-X-62,465 (1975).
Brown, "Theory and Application of Heated Films for Skin Friction Measurments," Proceedings of the 1967 Heat Transfer & Fluid Mechanics Institute (1967).
Bellhouse et al. "Determination of Mean and Dynamic Skin Friction, Separation and Transition in Low-Speed Flow with a Thin-Film Heated Element," J. Fluid Mech. (1966).
Bradshaw et al. "The Determination of Local Turbulent Skin Friction from Observation in the Viscous Sub-Layer," Aeronautical Research Council, Reports and Memorandum No. 3202 (1959).
Bellhouse et al. "The Measurement of Fluctuating Skin Friction in Air With Heated Thin-Film Gauges," J.Fluid Mech. (1968).

Primary Examiner—S. Clement Swisher
Attorney, Agent, or Firm—Brown & Martin

[57] ABSTRACT

A method and a gage for time-resolved skin-friction measurements. The gage is a composite structure comprised of a heated, flush-mounted, guard film and a hot wire mounted to an electrically insulated very low thermal conductivity material plug in the vicinity of the film and raised slightly above the plug surface. When the so constructed gage is calibrated in a laminar flow environment, it then has the ability to provide accurate readings of skin-friction in turbulent flow conditions.

53 Claims, 9 Drawing Figures

SKIN FRICTION GAGE FOR TIME-RESOLVED MEASUREMENTS

GOVERNMENT CONTRACT

This invention was made with Government support under Grant L NSG 3219 awarded by National Aeronautics and Space Administration. The Government has certain rights in this invention.

FIELD OF THE INVENTION

This invention relates generally to measurement devices and more particularly to a novel method and gage for accurately determining skin-friction or shear stress in turbulent flow conditions.

BACKGROUND OF THE INVENTION

A number of attempts have been made to accurately determine shear stress under turbulent flow conditions. These include the use of flush-mounted film gages and hot wires mounted in a number of locations including embedded in the surface to be tested or above that surface. It has been found that difficulties were encountered in calibrating these prior gages, so that in general they could not provide accurate readings of skin-friction in turbulent flows. The measurement of skin-friction in air by means of heated elements, surface gages or hot wires or films close to the wall is the subject of considerable research. Most of the previous work is concerned with the determination of mean skin-friction.

It is common knowledge that large fluctuations in skin-friction occur in turbulent flows. A relatively standard practice has been to calibrate instruments in a laminar flow of known characteristics and then apply the calibration results to sensor output in a turbulent flow to obtain shear stress readings. However, this procedure is known to be generally inaccurate when applied to many types of skin-friction gages. The assumption of the applicability of the laminar flow calibration to turbulent flow gives incorrect answers for skin-friction. As a matter of fact, for some types of prior art probes it has been found that the calibration of the probes in laminar flow cannot be used to obtain even the mean shear stress in a turbulent flow. Other studies have shown that the correct results for mean shear can be obtained only when a pseudo-calibration is performed. In this technique, which is termed a "turbulent calibration," the mean sensor output is determined when the mean skin friction is known, for example, when the probe is mounted in turbulent channel flow so that the mean pressure gradient determines the mean wall shear. The resulting calibration curve is interpreted in terms of the mean skin-friction. This procedure has significant limitations. It provides a method for obtaining mean data only in turbulent flows with a similar turbulent structure and is widely used therefor, but it is not generally satisfactory for obtaining accurate time-resolved skin-friction data.

An important difficulty in application of a laminar flow calibration to the measurement of either the mean or the time resolved skin-friction, relates to the temperature distribution in the wall in the immediate vicinity of the sensor and to the influence of that distribution on the sensor output. The extent of that influence depends on the thermal properties of the wall and on the detailed design of the gage. This difficulty has several manifestations. One of them is that the response of the wall to the spectrum of fluctuations in wall shear in a turbulent flow results in a mean temperature distribution in the wall which can differ from that in a laminar flow with a shear stress equal to the mean turbulent shear. This influence of the thermal field in the wall on the sensor is evident from testing which shows that in a laminar flow the effect of the wall on the output of a hot wire can be represented by a constant heat loss independent of the shear. In a turbulent flow, with the wire mounted sufficiently close to the wall so that it is within the viscous sublayer, it appears that the heat loss to the wall for a given mean shear is different from that measured in a laminar flow at that same shear. This result is consistent with the fact that the determination of even mean skin-friction in turbulent flows requires a "turbulent calibration," as mentioned above.

A second manifestation of the influence of wall temperature on sensor output relates to the interaction between the thermal field of the sensor and the linear velocity profile prevailing near the wall in laminar flow and in the viscous sublayer in a turbulent flow. When hot wire/films are used as skin-friction gases, they must be sufficiently close to the wall so that for the maximum shear stress to be measured they are well within the viscous sublayer.

Another manifestation of the influence of the wall on sensor output is the relatively long response time of the wall temperature to changes in heat transfer as a consequence of changes in wall shear. The combination of sensor and wall must be considered a single unit insofar as frequency response is concerned. The consequent degraded frequency response of gages using flush-mounted films and embedded wires makes them difficult to apply for time-resolved measurements. If by proper design the extent of the thermal field in the wall surrounding such sensors is made suitably small, laminar calibration of these gages can lead to accurate measurements of the mean turbulent shear stress, but this feature alone does not assure accuracy of time resolved data.

It has long been known to embed a hot wire in a plug of low thermal diffusivity for the measurement of mean shear stress. It is argued that the use of a material with such a property reduces the heat loss to the surrounding wall and thus the influence of the temperature field in the wall on the sensor output as well. Another alternative in this general structure is to employ an air gap between a flush-mounted film and the surrounding wall.

In the calculations required for calibrating a skin-friction instrument, it has been found that it is necessary to determine a fictitious length L associated with a particular gage operated under particular conditions. This length is defined as the length of wall on which a constant wall temperature would reproduce the actual heat loss associated with the distributed wall temperature. The length L can be considerably greater than either the streamwise dimension of a film or the diameter of a wire/film adjacent to the wall. It appears that one criterion for obtaining from a laminar calibration the correct mean turbulent shear stress is that the effective length of the gage be small.

Relatively little quantitative information is available concerning the frequency response characteristics of skin-friction gages. There is evidence to show that flush-mounted films possess complex low frequency characteristics due to their thermal interaction with the supporting substrate. It appears that certain of the flush-mounted gage structures have small effective lengths. A gage with a small effective length mounted in a material with a small thermal diffusivity may have an adequate frequency response but sufficient information is not available.

In skin-friction gages comprising hot wires/films mounted close to the wall, heat transfer from the sensor to the wall leads to altered sensor output and to failure of a laminar calibration to provide accurate mean turbulent shear stress. However, it appears that the frequency response of such gages is not seriously degraded by the interaction of wall and sensor.

SUMMARY OF THE INVENTION

A primary purpose of this invention is to provide a single gage for skin-friction measurements in turbulent flows. The gage, with appropriate apparatus, provides direct readouts of time-resolved measurements, the gage having been calibrated under laminar flow conditions.

The invention comprises a hot wire in the immediate vicinity of a flush-mounted film which serves as a guard heater where the film operates at a sufficiently high overheat so that the wall temperature influencing the wire output is effectively invariant. Both heated elements are operated in a constant temperature mode where the temperature of the film dominates the heat transfer between the wire and the wall. This structure provides the gage which is immune to changes in wall temperature and at the same time possesses appropriate frequency response.

The film and the wire sensors are each connected in one arm of a Wheatstone bridge of a constant temperature anemometer. The bridge output is proportional to the voltage necessary to maintain constant temperature. That voltage output is applied to a computation and memory means previously programmed with calibration information, the output of which is applied to a readout device which shows instantaneous shear stress.

BRIEF DESCRIPTION OF THE DRAWING

The objects, advantages and features of this invention will be more readily appreciated from the following detailed description when read in conjunction with the accompanying drawing in which.

DESCRIPTION OF THE PREFERRED EMBODIMENT

Figure 1:
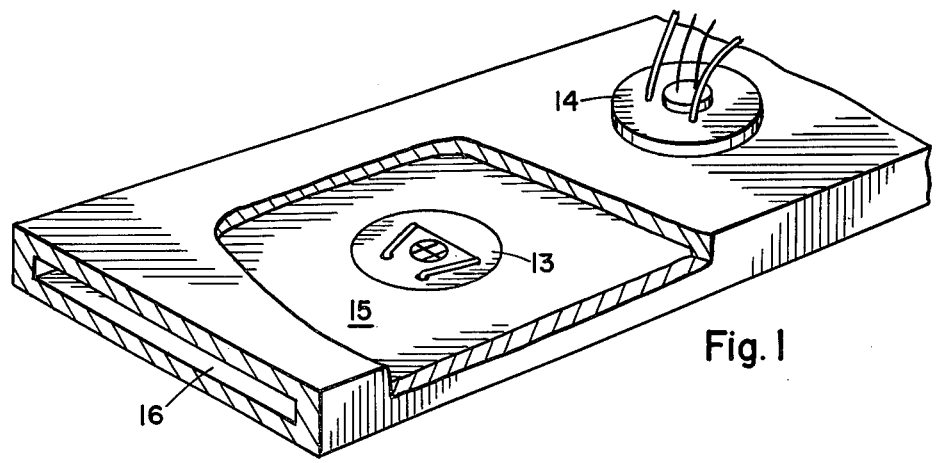
FIG. 1 is a perspective, partially broken away view of an elongated channel with several gages constructed in accordance with this invention mounted in the channel walls.
Figure 2:
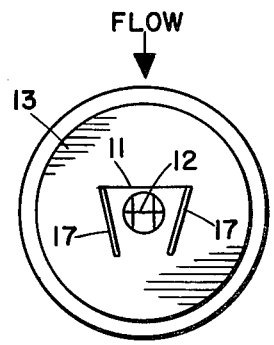
FIG. 2 is a top view of a gage constructed in accordance with the invention.
Figure 3:
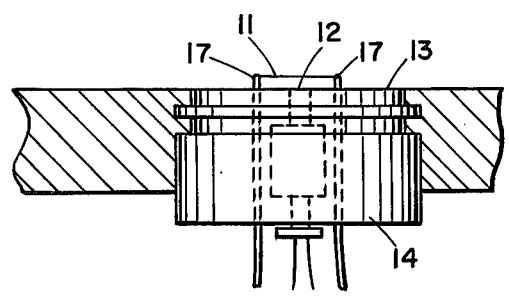
FIG. 3 is a side view of the sensor of FIG. 2.

With reference now to the drawing and more particularly to FIGS. 1-3, the gage of this invention employs a platinum-coated tungsten wire 11 positioned upstream of flush-mounted film gage 12, both mounted on or close to top surface 13 of phenolic plug 14. The phenolic plug is carefully machined so that surface 13 fits flush with the inner surfaces, such as surface 15, of the walls of channel 16. The channel configuration is not necessary for gage use, but is useful for calibration purposes.

By way of specific example but without limitation, wire 11 is $3.8 \times 10^{-3}$ mm in diameter, 1.27 mm long, located approximately $2.5 \times 10^{-2}$ mm above the wall or the surface 13 and is placed approximately $7.5 \times 10^{-2}$ mm upstream from flush-mounted film 12. With a length-to-diameter ratio of over 300, the influence of supporting needles 17 on wire 11 is negligible. An example of the flush-mounted film is a sensor made of nickel deposited on the flat face of a cylindrical quartz rod and is made by DISA Electronics. The film is 0.2 mm long in the streamwise direction, and 0.75 mm wide. It is protected by a quartz coating approximately 0.5 $\mu$m thick. These specifications are for information only, it being a requirement that the wire sensor be positioned within the thermal field of influence of the film sensor.

For purposes of generalization, with respect to dimensions and relationships, certain observations are useful. The wire probe must be above the wall surface, but there is some tolerance in its location. The wire probe can be located at $0 < y_w < y^*$ where $y_w$ is the height of the wire above the wall and $y^*$ is the thickness of the viscous sublayer. Thus it need only be located somewhere within the sublayer. As to the distance of the wire upstream from the film, it could be directly above the film or somewhat upstream, it only being necessary that it be within the thermal field of the film. The wire diameter can vary as long as its length to diameter ratio is large (approximately 300), its length is small compared with the thickness of the viscous sublayer, being of the same order or smaller than the length of the film, and it obeys all of the criteria discussed herein. Although gage and channel surfaces are shown planar, it is only necessary that they be smooth. The could be rounded cylindrically or spherically.

From a laminar flow calibration it was determined that the effective length of heated wire 11 is $8.33 \times 10^{-4}$ m, indicating that the gage is capable of measuring shear stress up to 0.9N/m². Higher shear stress values can, of course, be measured if the effective length of the wire is reduced, the smallest effective length being the wire diameter itself. It should be noted that electronic noise corresponds to a minimum measurable shear stress of 0.01N/m². However, it is contemplated that the shear stresses to be measured by this gage will be no greater than 0.1N/m². Also implied by this large value of permissible shear stress is an insensitivity of the wire output to alterations of the velocity profile as a consequence of streamwise pressure gradient.

Figure 4:
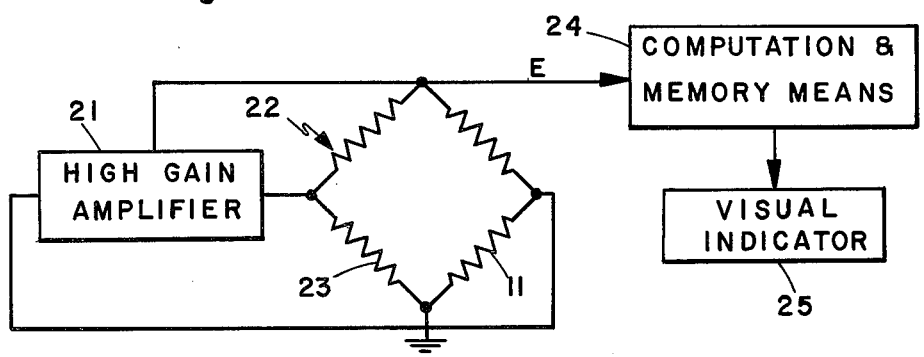
FIG. 4 is a schematic diagram of the circuitry and instrumentation in which the sensors of the gage of FIG. 2 are connected.
Figure 5:
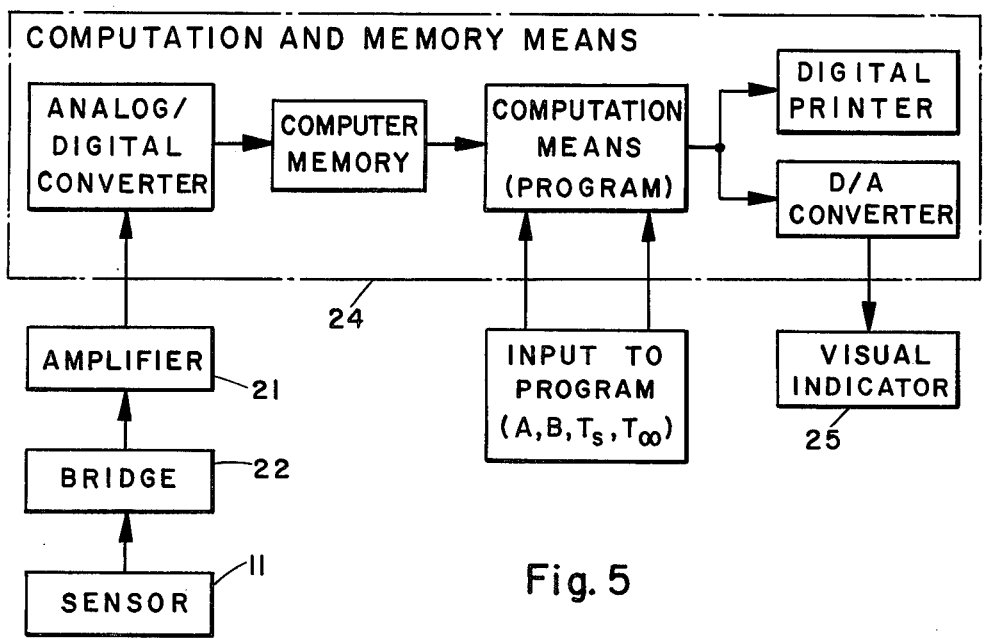
FIG. 5 is a block diagram of the apparatus of FIG. 4 showing in greater detail the computation and memory means.

The apparatus in which sensor 11 is connected and which provide the visual indications of skin-friction includes a constant temperature anemometer schematically shown in FIGS. 4 and 5. Film probe 12 is connected in a bridge in known manner and is merely maintained at a constant temperature. These instruments measure fluid flow parameters by sensing the heat transfer rate (heat flux) between an electrically heated sensor and the flow of the medium. The basic signal depends on the fluid composition, mass flow, shear stress and temperature difference. When temperature, shear stress or composition varies, the feedback circuit in the bridge varies the bridge voltage so as to maintain a constant sensor temperature. Specifically, the wire sensor is heated by current applied to bridge 22, one leg of which is sensor 11 and another of which is a control resistor 23. The control resistor is employed to set the sensor operating temperature. The basic output signal E of the bridge is a voltage which is related to flow approximately as follows:

$$E^2 = [A + B\tau_w^{\frac{1}{3}}][T_s - T_\infty] \quad (1)$$

where
A and B are constants depending on fluid properties,
$\tau_w$ is the shear stress or skin-friction at the wall,
$T_s$ is sensor operating temperature, and
$T_\infty$ is fluid or environmental temperature.

As flow increases the sensor tends to cool causing an off-balance of the bridge. This off-balance is immediately sensed by the amplifier which feeds back more current to bring the bridge back into balance. In this way, the sensor is controlled at a certain resistance (hence temperature) that depends on the value of the control resistor in the opposite leg of the bridge. The computation and memory means 24, which includes analog/digital converters, is programmed with the information determined from calibration of the instrument so that the bridge output E, when applied to computation and memory means 24, provides an output to a visual indicator 25, such as a digital readout device for a direct reading of skin-friction or shear stress. The computer program can be made to produce time resolved shear stress, mean and rms shear stress, power spectrum and probability density function. The computation and memory means are well within the state of the art and need not be further described herein. The same is also true of visual indicator 25.

The gage was calibrated in a fully-developed laminar flow within a two-dimensional duct which is 2.44 m long and 0.112 m wide with a 2.54 mm gap. Turbulent measurements including time-resolved data on skin-friction were carried out with the gap between the plates increased to 19.0 mm. The temperature of the air was measured with a thermistor and was maintained within 0.1° C. by means of a heat exchanger during test procedures. Typical fluid temperatures range from 10° C. to 50° C. For calibration purposes, several small openings were made in the sides of the duct for pressure and shear stress measurements to ensure close correlation between shear stress and pressure values. Pressure measurements are made with a MKS Baratron. The pressure gradient dp/dx which is obtained from a least square fit of the pressure data is converted to the shear stress at the wall. Similarly, for turbulent flow, the mean pressure gradient dp/dx is also determined and converted to the mean shear stress. In the channel mentioned above for laminar flow it is possible to control the shear stress for calibration purposes. During calibration various flow rates are tested and pressure drop readings, dp/dx, are taken, which correspond to unique and different values of shear in accordance with the well known relationship $$\tau_w = \frac{h}{2} \frac{dp}{dx}$$

where h is the channel height.

For constant temperature operation the theory of heated elements indicates that Equation (1) applies. A and B are constants determined during calibration of the instrument and the temperature difference $(T_s - T_\infty)$ is introduced to account for variations between tests of the air temperature $T_\infty$ which is measured, typically, by means of a thermistor. In a laminar calibration the voltage squared from the wire, $E^2$, is measured for discrete values (about ten) of dp/dx which are converted to the corresponding values of $\tau_w^{\frac{1}{3}}$ over the range of shear stress of interest. Then Equation (1) is used to determine the values of A and B providing the best fit to the data points in a least square sense.

Two modifications of Equation (1), with A and B known from the laminar calibration, are then employed. In connection with measurements of time-resolved shear stress $$\tau_w = \frac{1}{B^3}\left[\frac{E^2}{T_s - T_\infty} - A\right]^3 . \quad (2)$$

Thus values of the sensor voltage are input to computation and memory means 24 such as a micro computer with appropriate software to implement Equation (2) to obtain the corresponding values of $\tau_w$. The gage can then be used in uncontrolled situations to make measurements of shear stress. A program in the computation and memory means, having the values of A and B in memory correlated with values of $T_s - T_\infty = \Delta T$ determined during calibration, solves Equation (2) point by point and couples the results to an appropriate output device. Just as easily mean shear stress can be determined by averaging instantaneous values of $\tau_w$ over the period of time of interest. To assess the accuracy with which the mean turbulent shear stress is given by the laminar calibration, the mean of Equation (2) is determined $$\bar{\tau}_w = \frac{1}{B^3}[\overline{\epsilon^3} - 3A\,\overline{\epsilon^2} + 3A^2\,\overline{\epsilon} - A^3] \quad (3)$$

where $\epsilon = E^2/(T_s - T_\infty)$.

In this case the time series of the digital voltages are used to calculate the various moments $E^6$, $E^4$, etc., and the corresponding mean shear stress $\tau_w$. This calculated value, denoted $\tau_{w,gage}$, is compared with the value determined from the mean pressured gradient, denoted $\tau_{w,pg}$. This relationship is reflected in the graph of FIG. 6. The mean shear stress according to the gage of this invention is plotted against the mean shear stress determined from pressure measurements. Note that the plot is linear and at a 45° angle, indicating a one-to-one relationship between the gage reading and the corresponding mean shear stress determined from pressure measurements. This confirms the accuracy of the gage of this invention when measuring mean turbulent shear stress subsequent to laminar calibration.

In operation it has been found that this gage operates satisfactorily when the overheat ratio of the hot wire is 1.15 and the overheat ratio of the guard heating film is 1.4, but other overheat ratios would function satisfactorily. The overheat ratio used in this context corresponds to the ratio of the operating resistance (hot resistance) $R_H$, to the resistance of the sensor $R_c$, at ambient air temperature $T_\infty$. For small temperature differences it is well known that $$R_H = R_c(1 + \alpha(T_s - T_\infty)) \quad (4)$$

where $\alpha$ is the temperature coefficient of resistivity of the material and $T_s$ is the operating or hot temperature of the sensor. Thus the hot or operating temperature of the sensor can be obtained from Equation 4 from $$T_s = \frac{1}{\alpha}\left(\frac{R_H}{R_c} - 1\right) + T_\infty \quad (5)$$

where $R_H/R_c$ is the overheat ratio.

It is contemplated that the film overheat ratio could range from 1.2 to 1.65 and the wire overheat ratio could be 1.05 to 1.4. Note that the film is at a higher temperature, which is commensurate with its function as a guard heater for the wire. By positioning the wire within the thermal field of influence of the film, the wire is immunized from influences of the temperature distribution in the wall.

Figure 6:
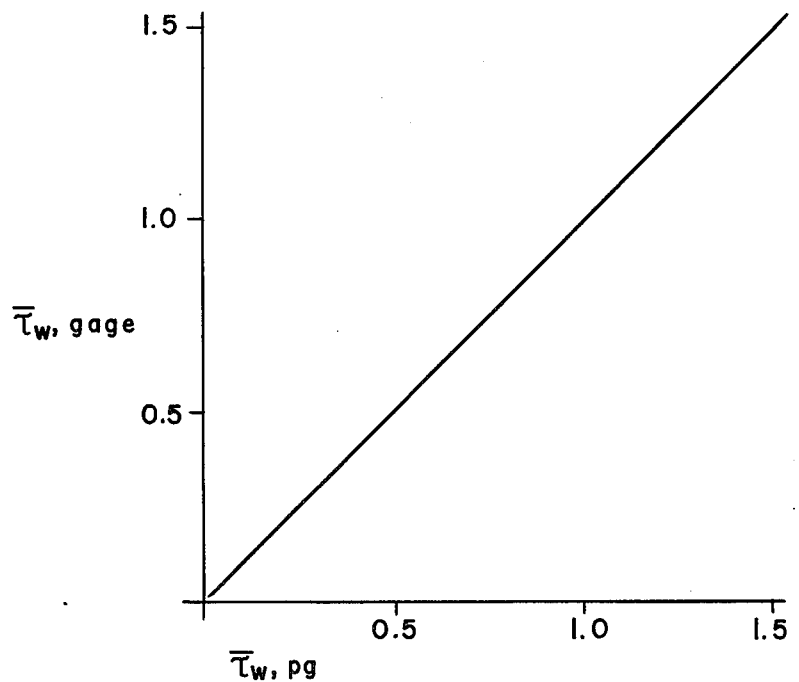
FIG. 6 is a graph of mean shear stress readings obtained by the gage plotted against those determined from pressure gradient values.

In calibrating the present instrument, several other sensors, calibrated similarly, were tested for comparison. These included a hot wire probe without guard heating with an overheat ratio of 1.15 and another one with an overheat ratio of 1.5, a cylindrical film and a flush-mounted film at an overheat ratio of 1.4, and finally the hot wire with guard heating according to the present invention, with the wire and film having overheat ratios of approximately 1.15 and 1.4 respectively. It was found that only this gage accurately yields the mean turbulent shear stress as indicated by FIG. 6 and that it does so throughout the range of shear stress of interest. The inaccuracies of the other gages were in qualitative agreement with the earlier results of similar nature discussed above, results which lead to the use of "turbulent calibrations." It should be pointed out here that the overheat ratio combination for the wire and film is not limited to 1.15 and 1.4 respectively. For example, given a film overheat ratio of 1.4, the wire can be set at any overheat ratio greater than 1.0 as long as the criteria for heated elements, discussed earlier, are met. Similarly, for a given wire overheat ratio of, for example, 1.15, a number of overheat ratios for the film greater than 1.15 can be used as long as its design maximum temperature is not exceeded and its thermal field is large enough to influence the wire output. Another overheat ratio actually tested and found to perform successfully is 1.08 and 1.65 for the wire and film, respectively.

Experimental data concerning frequency response indicates that the present gage is satisfactory over the frequency range of interest.

For time-resolved turbulent data, measurements were made in a fully developed turbulent channel flow at a Reynolds number of $1.34 \times 10^4$. The bulk average velocity across the channel at this Reynolds number is 11.0 m/s.

A segment of the time series of the shear stress at the wall is shown in FIG. 6. There are extended periods of relatively low and nearly constant shear stress between periods of high fluctuation intensity. The intermittent nature of the shear stresses confirms earlier studies. The level of the shear stresses during the relatively quiescent periods vary roughly in the range of $4-6 \times 10^{-2} N/m^2$ while the overall mean shear stress is found to be $7.02 \times 10^{-2} N/M^2$. It was also found that the shear stress during the quiescent periods varied slightly about a value less than that for a fully developed, laminar channel flow at the same Reynolds number, that shear stress value being $6.42 \times 10^{-2} N/M^2$.

Figure 7:
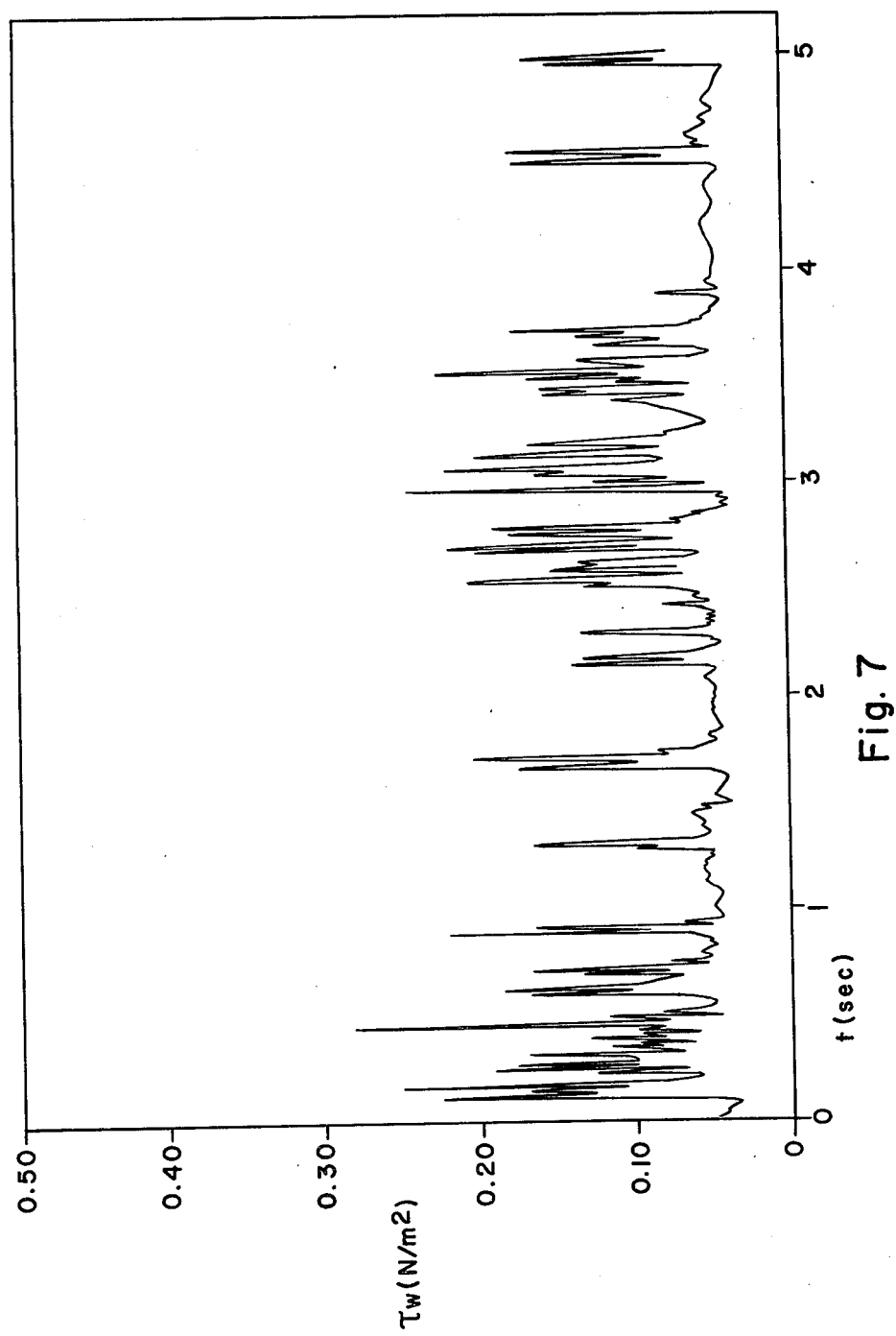
FIG. 7 shows a segment of the time series of the shear stress at the wall.

In other observation from the data produced by means of the instrument of the present invention the quiescent periods as shown in FIG. 7 are generally terminated by a sharp decrease in skin-friction followed by a sharp increase and intense fluctuation. This behavior is also consistent with earlier studies where it has been shown that turbulent boundary layer bursts of intense turbulence from the viscous sublayer are preceded by a region of slowly moving fluid and thus presumably by a low shear stress. The results of actual tests of the gage of this invention confirms many of the characteristics of wall shear in turbulent flows expected from the earlier studies of this phenomenon using other techniques.

Figure 8:
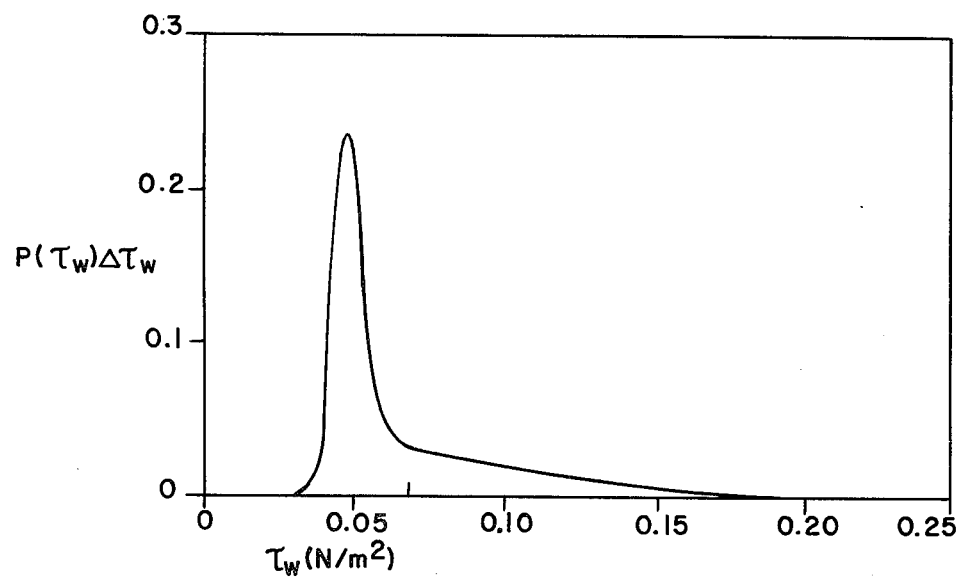
FIG. 8 is a plot of the probability density function for the shear stress.

The probability density function for the shear stress in this example is shown in FIG. 8. This distribution corresponds to a relative intensity of 0.46 but is seen to be highly skewed toward large values of the shear. The skewness factor is found to be 1.35, a value consistent with the time history of the shear stress seen in FIG. 7 and with the probability density function.

Figure 9:
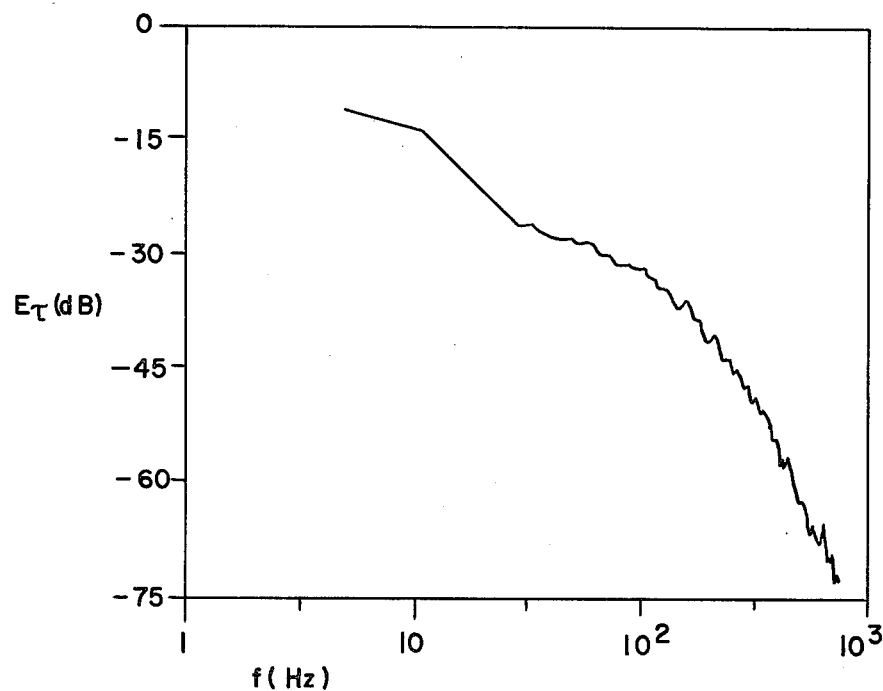
FIG. 9 is a graph of the power spectral density of the wall shear stress.

The power spectral density of the wall shear stress is presented in FIG. 9. This curve shows that there is significant energy in the fluctuations of the shear stress at frequencies up to 100 Hz with no evidence of noise even at the maximum frequency of 640 Hz, a result which implies that this gage is capable of resolving small scale fluctuations in the shear stress.

Experimental results from outputs of this gage as described above and shown in the drawing provide timeresolved data on the wall shear stress in a turbulent channel flow. Examination of the time series of the shear stress permits identification of the various phenomena associated with unsteadiness in the viscous sublayer. The results of experimental data clearly show that the gage of this invention provides for a useful range of shear stress time-resolved data in turbulent flows. Once calibrated, this gate is transportable to other loci for use in determining skin-friction for various flows under different test conditions. The hot wire mounted at a suitable small distance from the wall and made immune from the effect of fluctuations in the wall temperature by means of the guard heating film provides a gage which for the first time permits accurate determination of the instantaneous shear stress as well as spectral information of the flow, and from those readings it is easy to determine mean shear stress over any period of time desired. Mean shear stress is the time average $(\bar{\tau}_w)$ of the instantaneous shear stress $$\bar{\tau}_w = \lim_{T \to \infty} \frac{1}{T} \int_{t_0}^{t_0 + T} \tau_w(t)dt \quad (6)$$

where T is the averaging time and $t_0$ is the time at which averaging starts. From the instrumentation response, the form of the power spectrum and the fact that the mean shear stress is correctly measured (FIG. 6), it is evident that this gage accurately measures instantaneous shear stress.

In view of the above description, it is likely that modifications and improvements will occur to those skilled in the art to which this invention pertains which are within the scope of the appended claims.

What is claimed is:

1. A method of determining time-resolved measurements of skin-friction in turbulent fluid flow, said method comprising the steps of:
   forming a composite gage by mounting a film probe and a wire probe on a smooth surface of an electrically insulated plug of low thermal conductivity, said film probe being flush with said surface, said wire probe being positioned slightly above said surface but within the thermal field of influence of said film;
   connecting each said probe in a respective bridge circuit having means connected thereto to maintain the temperature of each said probe substantially constant;
   mounting said composite gage in the wall of a calibration channel having known laminar flow characteristics and controlled values of skin-friction;
   determining the voltage output of said wire probe bridge circuit necessary to maintain constant wire probe temperature;
   relating said voltage output to known values of skin-friction in said laminar flow channel;
   determining from the laminar flow information the constants A and B in the equation $$E^2 = [A + B\tau_w^{\frac{1}{3}}][T_s - T_\infty]$$

where E is the bridge output voltage,
   $\tau_w$ is the shear stress or skin-friction at the wall,
   $T_s$ is the probe temperature, and
   $T_\infty$ is the temperature of the flowing fluid;
   entering the values of said constants A and B in computation and memory means, together with algorithms necessary to relate bridge output voltage E and $\Delta T(T_s - T_\infty)$ and the values of said constants to shear stress according to the relationship $$\tau_w = \frac{1}{B^3}\left[\frac{E^2}{T_s - T_\infty} - A\right]^3;$$

removing said gage from said calibration channel;
   mounting said gage in a wall to be tested with said surface flush with the wall surface of interest;
   providing indicating means connected to the output of said computation and memory means to indicate instantaneous shear stress at the wall under test in turbulent flow;
   providing turbulent fluid flow over the wall surface to be tested; and
   measuring values of skin-friction with said calibrated gage.

2. The method recited in claim 1 wherein said wire probe is above said surfaces within the viscous sublayer of the flowing fluid.

3. The method recited in claim 2 wherein said wire probe is directly above or upstream from said film probe.

4. The method recited in claim 3 wherein said wire probe is maintained at a temperature above the fluid flow temperature.

5. The method recited in claim 4 wherein said film probe is maintained at a temperature above the temperature of said wire probe.

6. The method recited in claim 3 wherein said film probe is maintained at a temperature above the temperature of said wire probe.

7. The method recited in claim 2 wherein said wire probe is maintained at a temperature above the fluid flow temperature.

8. The method recited in claim 7 wherein said film probe is maintained at a temperature above the temperature of said wire probe.

9. The method recited in claim 2 wherein said film probe is maintained at a temperature above the temperature of said wire probe.

10. The method recited in claim 1 wherein said wire probe is directly above or upstream from said film probe.

11. The method recited in claim 10 wherein said film probe is maintained at a temperature above the fluid flow temperature.

12. The method recited in claim 11 wherein said wire probe is maintained at a temperature above the fluid flow temperature.

13. The method recited in claim 10 wherein said wire probe is maintained at a temperature above the fluid flow temperature.

14. The method recited in claim 1 wherein said wire probe is maintained at a temperature above the fluid flow temperature.

15. The method recited in claim 14 wherein said film probe is maintained at a temperature above the temperature of said wire probe.

16. The method recited in claim 1 wherein said film probe is maintained at a temperature above the temperature of said wire probe.

17. The method recited in claim 1 wherein said wire has a length to diameter ratio of about 300.

18. The method recited in claim 17 wherein said constant temperture anemometer comprises a bridge with feedback amplifier.

19. The method recited in claim 1 wherein said temperature maintaining means comprises a constant temperature anemometer.

20. A gage for time-resolved measurements of skin-friction in turbulent fluid flow, said gage being connected with appropriate bridge circuitry, a constant temperature anemometer, computation and memory means and indicating means to provide instantaneous skin-friction readings when said gage is mounted in a surface under test, said gage comprising:
   an electrically insulative plug of low thermal conductivity having at least one smooth surface;
   a film probe mounted flush with said surface;
   means for connecting said film probe in said bridge circuitry so as to maintain the temperature of said film probe substantially constant;
   a wire probe mounted slightly above said planar surface but within the thermal field of influence of said film;
   means for connecting said wire probe in said bridge circuitry and to said constant temperature anemometer so as to maintain the temperature of said wire probe substantially constant; and
   said plug being adapted to be mounted in a wall with said surface flush with the wall surface under test; whereby when said gage is so mounted in said wall and connected in said circuitry, said indicating means provides indication of instantaneous skin-friction with a turbulent fluid flow passing across said wall surface.

21. The gage recited in claim 20 wherein said wire probe is above said surface within the viscous sublayer of the flowing fluid.

22. The gage recited in claim 21 wherein said wire probe is directly above or upstream from said film probe.

23. The gage recited in claim 22 wherein said wire probe is maintained at a temperature above the fluid flow temperature.

24. The gage recited in claim 23 wherein said film probe is maintained at a temperature above the temperature of said wire probe.

25. The gage recited in claim 22 wherein said film probe is maintained at a temperature above the temperature of said wire probe.

26. The gage recited in claim 21 wherein said wire probe is maintained at a temperature above the fluid flow temperature.

27. The gage recited in claim 26 wherein said fluid probe is maintained at a temperature above the temperature of said wire probe.

28. The gage recited in claim 21 wherein said film probe is maintained at a temperature above the temperature of said wire probe.

29. The gage recited in claim 20 wherein said wire probe is directly above or upstream from said film probe.

30. The gage recited in claim 29 wherein said film probe is maintained at a temperature above the temperature of said film probe.

31. The gage recited in claim 30 wherein said wire probe is maintained at a temperature above the fluid flow temperature.

32. The gage recited in claim 29 wherein said wire probe is maintained at a temperature above the fluid flow temperature.

33. The gage recited in claim 20 wherein said wire probe is maintained at a temperature above the fluid flow temperature.

34. The gage recited in claim 33 wherein said film probe is maintained at a temperature above the temperature of said wire probe.

35. The gage recited in claim 20 wherein said film probe is maintained at a temperature above the temperature of said wire probe.

36. The gage recited in claim 20 wherein said wire has a length to diameter ratio of about 300.

37. Apparatus for time-resolved measurements of skin-friction in turbulent flow, said apparatus comprising:
   a gage member comprising:
      an electrically insulated plug of low thermal conductivity having at least one smooth surface;
      a film probe mounted flush with said surface;
      a wire probe mounted slightly above said surface but within the thermal field of influence of said film;
   a first bridge circuit, said film being connected as one arm thereof;
   a second bridge circuit, said wire being connected as one arm thereof;
   first DC amplifier means connected across said first bridge, said first amplifier means being sensitive to temperature induced changes in the resistance of said film to maintain the temperature thereof substantially constant;
   second DC amplifier means connected across said second bridge, said second amplifier means being sensitive to temperature induced changes in the resistance of said wire to maintain the temperature thereof substantially constant;
   the output signal of said second bridge circuit being representative of the voltage necessary to maintain said wire probe at constant temperature;
   computation and memory means connected to said wire probe bridge circuit output, said computation and memory means being programmed with constants and algorithms to provide a unique output representative of instantaneous shear stress on said surface due to temperature changes of said wire probe caused by fluid flow across said surface; and
   indicator means connected to said computation and memory means to provide indication of instantaneous shear stress.

38. The apparatus recited in claim 37 wherein said wire probe is above said surface within the viscous sublayer of the flowing fluid.

39. The apparatus recited in claim 38 wherein said wire probe is directly above or upstream from said film probe.

40. The apparatus recited in claim 39 wherein said wire probe is maintained at a temperature above the fluid flow temperature.

41. The apparatus recited in claim 40 wherein said film probe is maintained at a temperature above the temperature of said wire probe.

42. The apparatus recited in claim 39 wherein said film probe is maintained at a temperature above the temperature of said wire probe.

43. The apparatus recited in claim 38 wherein said wire probe is maintained at a temperature above the fluid flow temperature.

44. The apparatus recited in claim 43 wherein said film probe is maintained at a temperature above the temperature of said wire probe.

45. The apparatus recited in claim 38 wherein said film probe is maintained at a temperature above the temperature of said wire probe.

46. The apparatus recited in claim 37 wherein said wire probe is directly above or upstream from said film probe.

47. The apparatus recited in claim 46 wherein said film probe is maintained at a temperature above the fluid flow temperature.

48. The apparatus recited in claim 47 wherein said wire probe is maintained at a temperature above the fluid flow temperature.

49. The apparatus recited in claim 46 wherein said wire probe is maintained at a temperature above the fluid flow temperature.

50. The apparatus recited in claim 37 wherein said wire probe is maintained at a temperature above the fluid flow temperature.

51. The apparatus recited in claim 50 wherein said film probe is maintained at a temperature above the temperature of said wire probe.

52. The apparatus recited in claim 37 wherein said film probe is maintained at a temperature above the temperature of said wire probe.

53. The apparatus recited in claim 37 wherein said wire has a length to diameter ratio of about 300.

* * * * *

UNITED STATES PATENT AND TRADEMARK OFFICE
CERTIFICATE OF CORRECTION

PATENT NO. : 4,475,392

DATED : October 9, 1984

INVENTOR(S) : Christopher O. Ajagu, Paul A. Libby & John LaRue

It is certified that error appears in the above-identified patent and that said Letters Patent are hereby corrected as shown below:

Column 9, line 33, change $$E^2 = [A + B\tau_w^{5/8}] [T_s - T_\infty] \quad \text{to}$$

$$E^2 = [A + B\tau_w^{1/3}] [T_s - T_\infty]$$

Signed and Sealed this

Twenty-fifth Day of June 1985

[SEAL]

Attest:

DONALD J. QUIGG

*Attesting Officer*   *Acting Commissioner of Patents and Trademarks*